US007731669B2

(12) United States Patent
Mathews et al.

(10) Patent No.: US 7,731,669 B2
(45) Date of Patent: Jun. 8, 2010

(54) GUIDEWIRE FORMED WITH COMPOSITE CONSTRUCTION AND METHOD FOR MAKING THE SAME

(75) Inventors: Eric D. Mathews, Walpole, MA (US);
Andrew M. Whitehead, Marshfield, MA (US); John R. Panicci, Plymouth, MA (US)

(73) Assignee: Concert Medical, LLC, Norwell, MA (US)

( * ) Notice: Subject to any disclaimer, the term of this patent is extended or adjusted under 35 U.S.C. 154(b) by 0 days.

(21) Appl. No.: 11/801,703

(22) Filed: May 10, 2007

(65) Prior Publication Data

US 2007/0282270 A1     Dec. 6, 2007

Related U.S. Application Data

(60) Provisional application No. 60/799,985, filed on May 12, 2006.

(51) Int. Cl.
  *A61B 5/00* (2006.01)
  *B21F 15/02* (2006.01)
  *F16B 2/02* (2006.01)
  *F16B 7/04* (2006.01)
  *F16D 1/02* (2006.01)

(52) U.S. Cl. .................. 600/585; 140/111; 403/311; 403/333; 403/334

(58) Field of Classification Search .......... 600/585; 140/111–122; 403/311, 333, 334
See application file for complete search history.

(56) References Cited

U.S. PATENT DOCUMENTS 5,109,867 A * 5/1992 Twyford, Jr. .......... 600/585

5,341,818 A    8/1994 Abrams et al.
5,720,300 A *  2/1998 Fagan et al. .......... 600/585
5,772,641 A *  6/1998 Wilson .......... 604/523

(Continued)

OTHER PUBLICATIONS

"Special Metals Nitinol Superelastic Ni-Ti Alloy." MatWeb Material Property Data. <www.matweb.com> Jan. 9, 2009. p. 1.*

(Continued)

*Primary Examiner*—Max Hindenburg
*Assistant Examiner*—John Pani
(74) *Attorney, Agent, or Firm*—Pandiscio & Pandiscio

(57) ABSTRACT

A composite guidewire comprising a proximal wire segment having a proximal end, a distal end and a longitudinal axis extending therebetween, the distal end being formed with a first flat planar bonding face which extends parallel to the longitudinal axis, the proximal wire segment having a first elasticity; a distal wire segment having a proximal end, a distal end and a longitudinal axis extending therebetween, the proximal end being formed with a second flat planar bonding face which extends parallel to the longitudinal axis, the distal wire segment having a second elasticity; wherein the first and second flat planar bonding faces of the proximal wire segment are formed complementary to one another; and further wherein the proximal and distal wire segments are joined together by bonding the first flat planar bonding face to the second flat planar bonding face in an overlapping manner and a method for forming a composite guidewire.

16 Claims, 22 Drawing Sheets

U.S. PATENT DOCUMENTS

| | | | |
|---|---|---|---|
| 5,853,375 A * | 12/1998 | Orr | 600/585 |
| 5,980,471 A | 11/1999 | Jafari | |
| 6,544,197 B2 | 4/2003 | DeMello | |
| 6,702,762 B2 * | 3/2004 | Jafari et al. | 600/585 |
| 6,918,882 B2 | 7/2005 | Skujins et al. | |
| 2004/0167443 A1 * | 8/2004 | Shireman et al. | 600/585 |

OTHER PUBLICATIONS

"Sandvik Bioline 1RK91 Precision Wire." MatWeb Material Property Data. <www.matweb.com> Jan. 9, 2009. pp. 1-2.*

"Carpenter MP35N* Ni-Co-Cr-Mo Alloy, 15% Cold Reduction." MatWeb Material Property Data. <www.matweb.com> Jan. 9, 2009. pp. 1-2.*

* cited by examiner

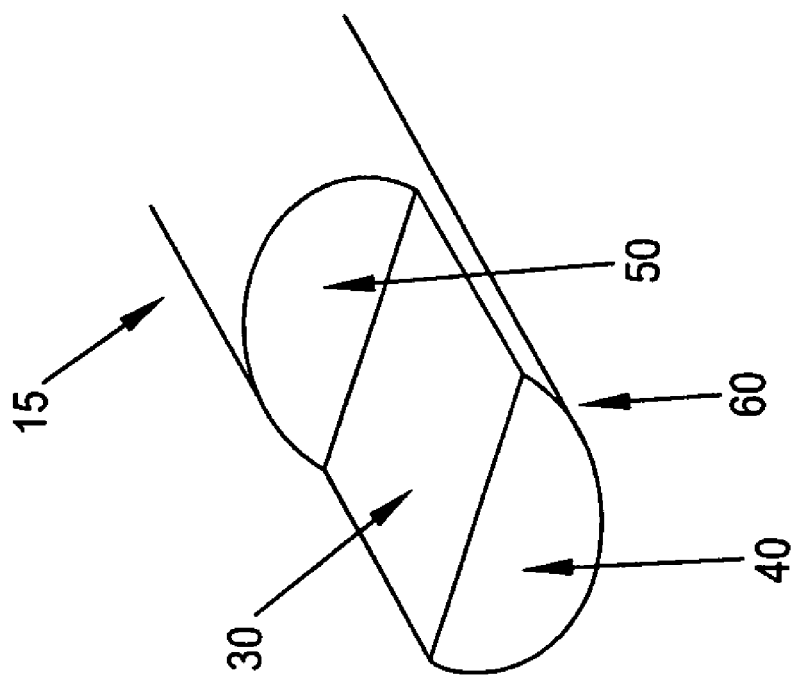
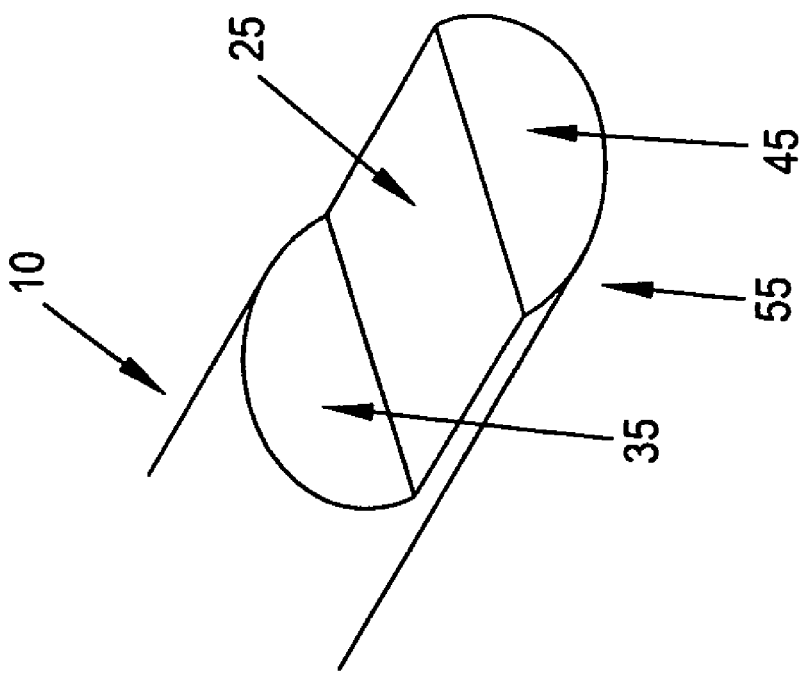
FIG. 2

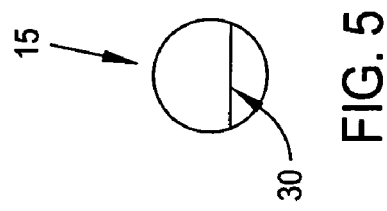
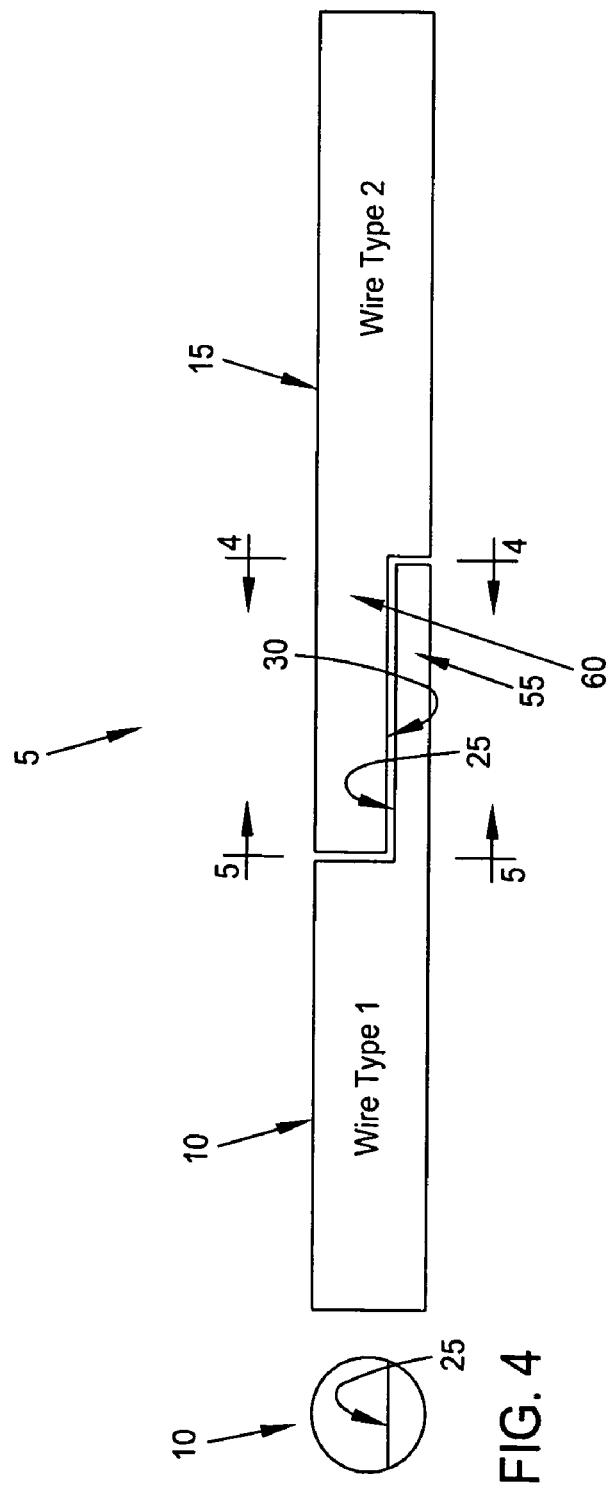
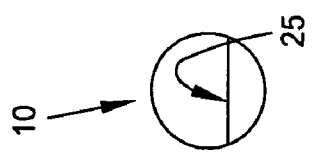
FIG. 5
FIG. 3
FIG. 4

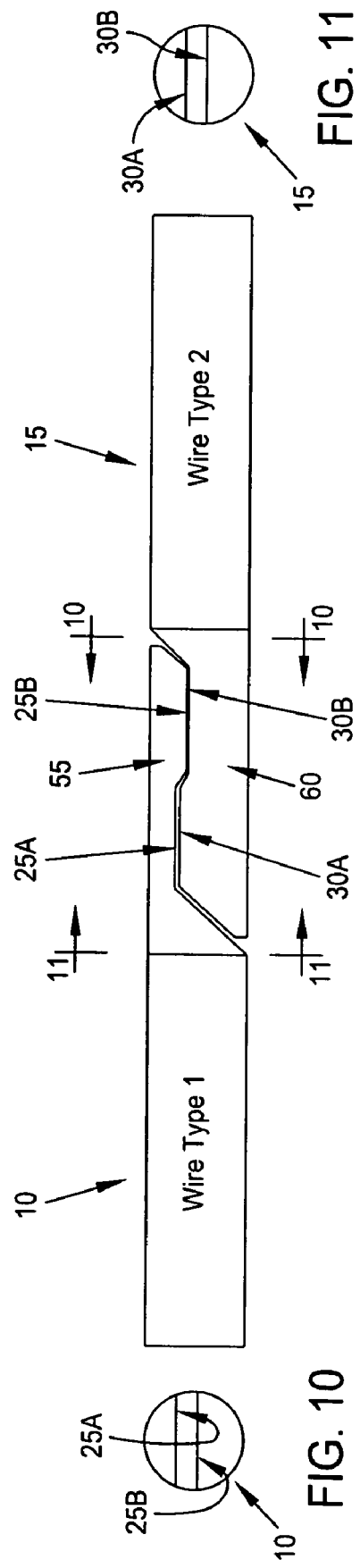

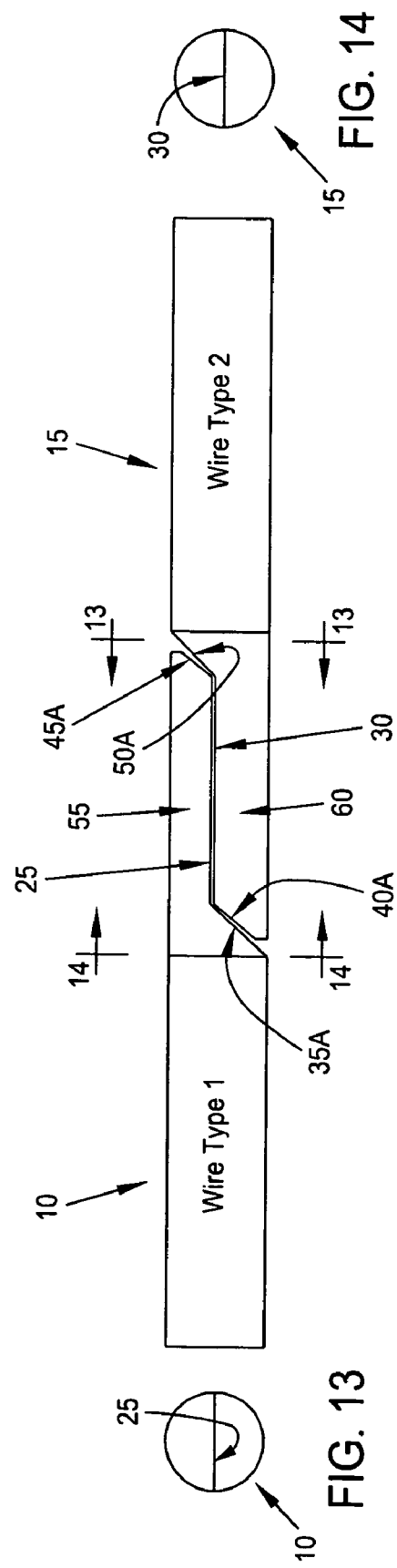

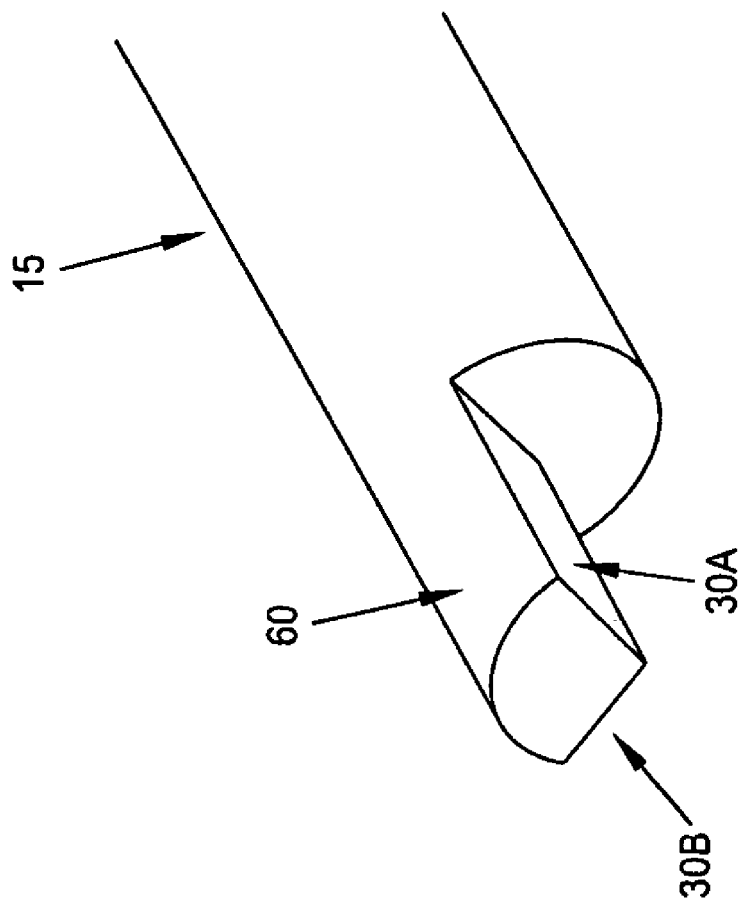
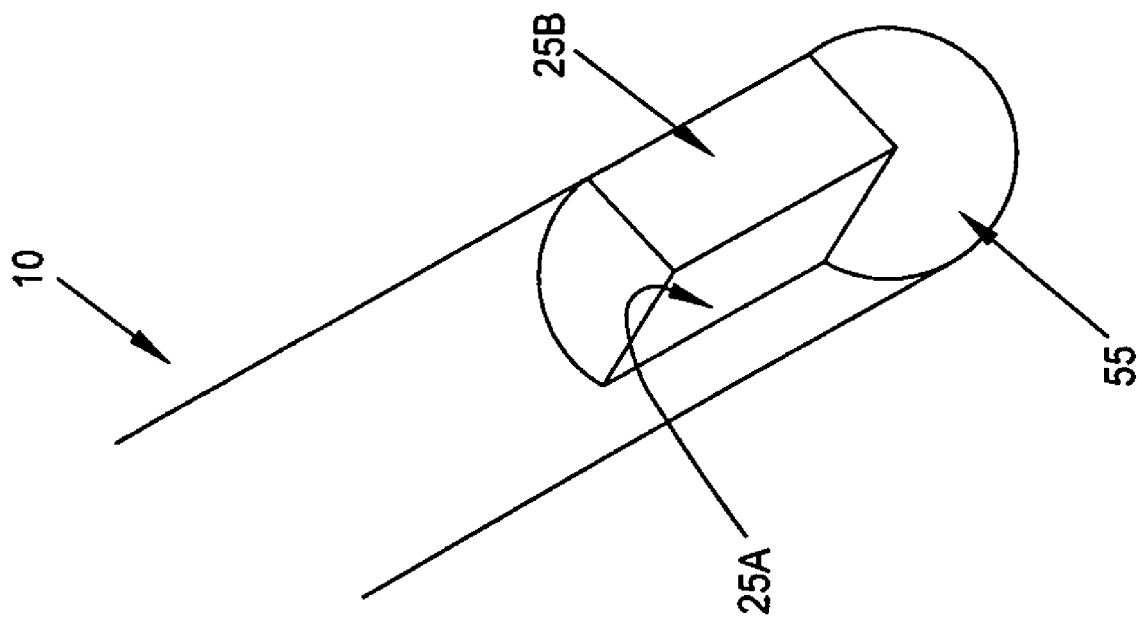
FIG. 25

GUIDEWIRE FORMED WITH COMPOSITE CONSTRUCTION AND METHOD FOR MAKING THE SAME

REFERENCE TO PENDING PRIOR PATENT APPLICATION

This patent application claims benefit of pending prior U.S. Provisional Patent Application Ser. No. 60/799,985, filed May 12, 2006 by Eric D. Mathews et al. for NOVEL COMPOSITE CONSTRUCTION AND METHOD FOR MAKING THE SAME, which patent application is hereby incorporated herein by reference.

FIELD OF THE INVENTION

This invention relates to medical apparatus and methods in general, and more particularly to medical guidewires and methods for making the same.

BACKGROUND OF THE INVENTION

Guidewires are widely used in medical procedures. Vascular guidewires, for example, are commonly used to guide catheters through tortuous vasculature to distal sites. By way of example but not limitation, a guidewire used for delivering coronary stents might enter the patient's body down at the femoral artery, traverse the intervening vasculature, and terminate in a coronary artery. An orthopedic arthroscopic guidewire, on the other hand, is commonly used to guide tools and/or implants through a keyhole incision and down to an internal surgical site, where the tools and/or implants are to be utilized.

The present invention is directed to vascular guidewires and the like, among other things.

Due to their application, vascular guidewires generally require different properties for different portions of the guidewire.

More particularly, the distal end of the guidewire generally requires higher elasticity and lower stiffness, in order to provide sufficient flexibility to navigate through highly tortuous anatomy. At the same time, the distal end of the guidewire still requires some stiffness, in order to maintain the torque transmission requirements of the guidewire and to provide sufficient support for stent delivery.

The proximal end of the guidewire generally requires lower elasticity and higher stiffness, in order to provide sufficient column strength to ensure adequate pushability of the guidewire through substantial vascular lengths and in order to provide adequate torque transmission along the guidewire. At the same time, the proximal end of the guidewire still requires some flexibility, in order to permit the guidewire to navigate through highly tortuous anatomy.

Due to the varying demands on various parts of the guidewire, it is generally desirable to utilize different materials to form different parts of the guidewire. Thus, in recent years, several types of "composite" guidewires have been developed. These composite guidewires are generally formed by joining two wire lengths, each wire length being made from a different material having different intrinsic properties. Typically, these composite guidewires utilize (i) stainless steel wire to form the proximal end of the guidewire, and (ii) nickel titanium (i.e., Nitinol) wire to form the distal end of the guidewire. By abutting these two different wire segments into a single contiguous guidewire, the properties of stainless steel (e.g., lower elasticity and higher stiffness) are provided at the proximal end of the composite guidewire, and the properties of nickel titanium (e.g., higher elasticity and lower stiffness) are provided at the distal end of the composite guidewire. Thus, superior pushability and torquability are provided in the proximal segment of the composite guidewire, and flexibility, durability and support are provided in the distal segment of the composite guidewire.

One consequence of replacing conventional, single-segment guidewires with composite, multi-segment guidewires is the introduction of a joint between adjoining segments of the composite guidewires. This joint can be problematic, inasmuch as it is imperative that the joint not undermine the integrity of the guidewire. In other words, it is important that the joint provide adequate (i) tensile strength, (ii) torque strength, (iii) bending moment performance, and (iv) failure mode characteristics, among other things. By way of example but not limitation, tensile strength is important since, if the guidewire becomes stuck during use, it may be necessary to pull the guidewire free.

In the prior art, a cylindrical coupler has generally be used to join together two wire segments each having circular cross-sections.

For example, U.S. Pat. No. 5,341,818 (Abrams et al.) discloses a connector made of Nitinol tubing which compresses inwardly onto the two wire segments so as to secure the joint.

U.S. Pat. No. 5,980,471 (Jafari) discloses a tubular connector which provides a mechanical interlock between the two wire segments, wherein the two wire segments are irregularly shaped and the space inside the tube is filled with solder or adhesive.

U.S. Pat. No. 6,544,197 (DeMello) also discloses a Nitinol tubing coupler, but additionally includes a safety wire in the joint to secure the two wire segments.

U.S. Pat. No. 6,918,882 (Skujins et al.) discloses a connector formed out of a nickel-chromium-molybdenum alloy, or a nickel-chromium-iron alloy, that is suitable for welding together the two wire segments.

None of the foregoing patents teach or suggest the novel composite guidewire disclosed herein, or the method for making the novel composite guidewire disclosed herein.

In addition to the foregoing, there are also many other types of wire-based surgical devices. By way of example but not limitation, these include other types of guidewires; snares; retrievers and graspers; embolic protection devices (e.g., filters); detachable devices that position embolic materials and implantable filters; biopsy devices; devices that deliver energy such as ultrasound, electric current, and radiofrequency; etc. These and other wire-based devices may require different performance characteristics along various segments of their length. By way of example but not limitation, a biopsy device might utilize a wire which requires the properties of titanium along one segment of the wire and the properties of a cobalt-chromium alloy along another segment of the wire. In fact, wire-based surgical devices frequently comprise multiple segments providing different functions, each of which might advantageously employ the differing properties of stainless steel, Nitinol, titanium, cobalt-chromium alloys, alloys based on the noble metals and various non-metallic composites.

Thus, in a further aspect of the present invention, the wire joining concepts of the present invention may be used to join different materials having desirable properties in a composite wire in order to achieve the performance characteristics desired for such other wire-based surgical devices.

SUMMARY OF THE INVENTION

The present invention provides a means for joining together two different wire segments at a joint that provides improved (i) tensile strength, (ii) torque strength, (iii) bending moment performance, and (iv) failure mode characteristics, among other things, and which is suitable for medical applications. More particularly, using advanced grinding technology or other suitable manufacturing techniques, complementary flat planar bonding faces, suitable for overlapping bonding, are created at the ends of the two wire segments which are to be joined. The complementary flat planar bonding faces are of sufficient surface area as to provide the required tensile strength and torque strength for the guidewire.

In one preferred form of the invention, each of the complementary flat planar bonding faces comprises a single surface. In another preferred form of the invention, each of the complementary flat planar bonding faces comprises a plurality of surfaces.

Gradual transitions may be added along the lengths of the wire segments so as to provide the required bending moment performance, e.g., the wire segments may be configured so as to provide a monotonic transition of the bending moment along the length of the composite guidewire.

Furthermore, the joint of the composite guidewire may be configured so as to provide the desired failure mode characteristics.

In one preferred form of the invention, there is provided a composite guidewire comprising:

a proximal wire segment having a proximal end, a distal end and a longitudinal axis extending between the proximal end and the distal end, the distal end of the proximal wire segment being formed with a first flat planar bonding face which extends parallel to the longitudinal axis, the proximal wire segment having a first elasticity;

a distal wire segment having a proximal end, a distal end and a longitudinal axis extending between the proximal end and the distal end, the proximal end of the distal wire segment being formed with a second flat planar bonding face which extends parallel to the longitudinal axis, the distal wire segment having a second elasticity;

wherein the second flat planar bonding face of the proximal wire segment is formed complementary to the first flat planar bonding face of the distal wire segment;

and further wherein the proximal wire segment is joined to the distal wire segment by bonding the first flat planar bonding face of the proximal wire segment to the complementary second flat planar bonding face of the distal wire segment in an overlapping manner.

In another form of the invention, there is provided a method for forming a composite guidewire, the method comprising the steps of:

providing a proximal wire segment having a proximal end, a distal end and a longitudinal axis extending between the proximal end and the distal end, the distal end of the proximal wire segment being formed with a first flat planar bonding face which extends parallel to the longitudinal axis, the proximal wire segment having a first elasticity;

providing a distal wire segment having a proximal end, a distal end and a longitudinal axis extending between the proximal end and the distal end, the proximal end of the distal wire segment being formed with a second flat planar bonding face which extends parallel to the longitudinal axis, the distal wire segment having a second elasticity;

wherein the second flat planar bonding face of the proximal wire segment is formed complementary to the first flat planar bonding face of the distal wire segment; and bonding the first flat planar bonding face of the proximal wire segment to the complementary second flat planar bonding face of the distal wire segment in an overlapping manner.

In another form of the invention, there is provided a composite wire comprising a first wire segment and a second wire segment, the first wire segment being joined to the second wire segment at bonded complementary flat planar bonding faces.

In another form of the invention, there is provided a method for forming a composite wire, the method comprising the steps of:

providing a first wire segment and a second wire segment;

providing a first flat planar bonding face on the first wire segment, and providing a complementary second flat planar bonding face on the second wire segment; and bonding the first flat planar bonding face of the first wire segment to the complementary second flat planar bonding face of the second wire segment in an overlapping manner.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like elements, and further wherein:

FIG. 2 shows the composite guidewire of FIG. 1, but with the two wire segments separated, and with one of the wire segments rotated 180 degrees, so as to expose their complementary flat planar bonding faces;

FIG. 3 is a view like that of FIG. 1, but showing another joint construction;

FIG. 4 is a sectional view taken along line 4-4 of FIG. 3;

FIG. 5 is a sectional view taken along line 5-5 of FIG. 3;

FIG. 9 is a view like that of FIG. 6, but showing another joint construction;

FIG. 10 is a sectional view taken along line 10-10 of FIG. 9;

FIG. 11 is a sectional view taken along line 11-11 of FIG. 9;

FIG. 12 is a view like that of FIG. 9, but showing another joint construction;

FIG. 13 is a sectional view taken along line 13-13 of FIG. 12;

FIG. 14 is a sectional view taken along line 14-14 of FIG. 12;

FIG. 25 is a schematic view showing another possible joint construction for the composite guidewire of the present invention;

DETAILED DESCRIPTION OF THE PRESENT INVENTION

Figure 1:
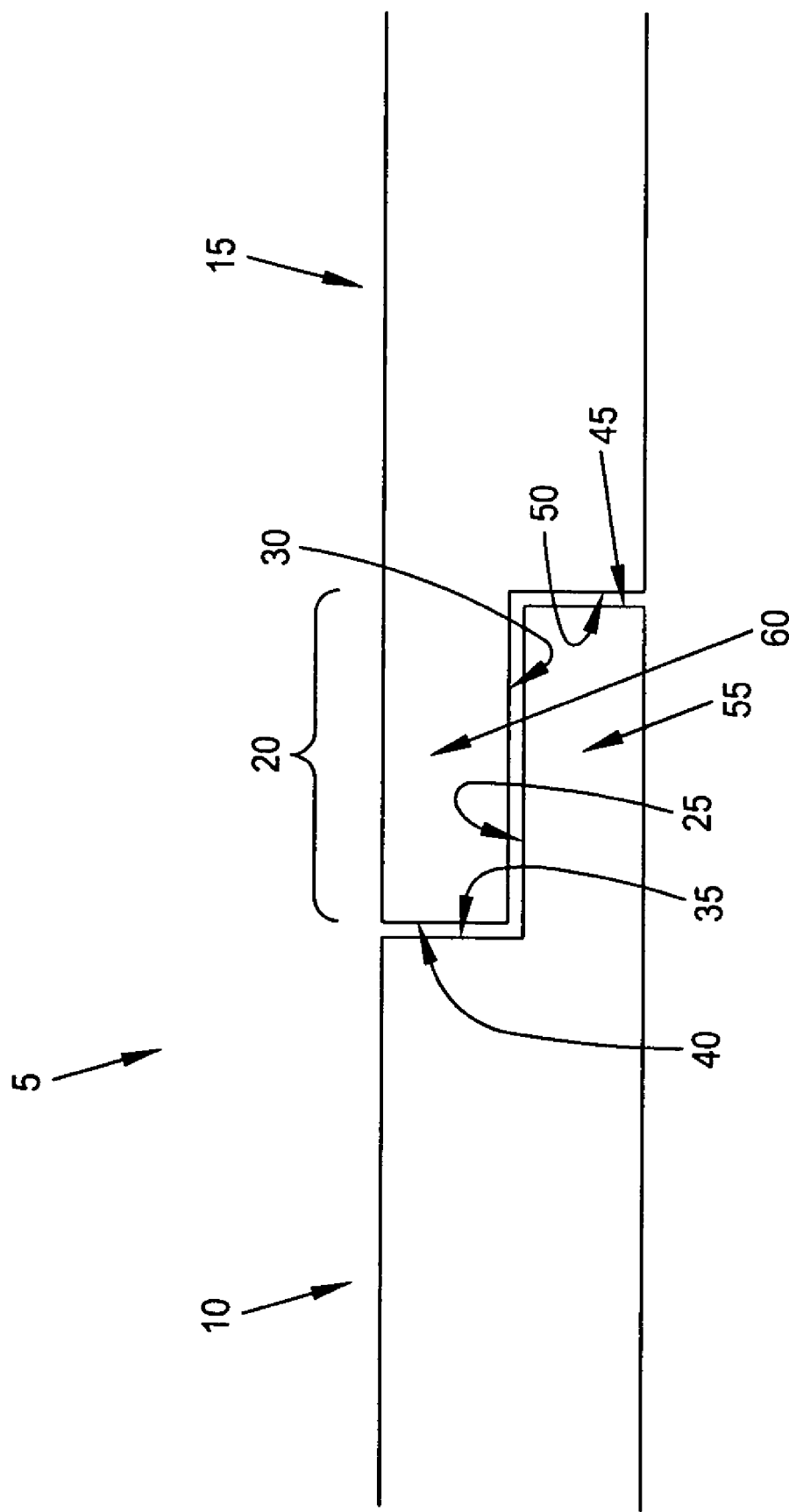
FIG. 1 is a partial side view showing a composite guidewire formed in accordance with the present invention, wherein the composite guidewire utilizes one preferred form of joint construction.

Looking first at FIGS. 1 and 2, there is shown a novel composite guidewire 5 formed in accordance with the present invention. Novel composite guidewire 5 generally comprises a first wire segment 10 and a second wire segment 15. First wire segment 10 and second wire segment 15 are attached to one another at a joint 20.

First wire segment 10 and second wire segment 15 are preferably formed out of different materials, in order to permit composite guidewire 5 to have different characteristics along its length.

In one preferred form of the present invention, composite guidewire 5 comprises a vascular guidewire, with first wire segment 10 comprising the proximal portion of the composite guidewire and second wire segment 15 comprising the distal portion of the composite guidewire. To this end, proximal wire segment 10 generally requires lower elasticity and higher stiffness, in order to provide sufficient column strength to ensure adequate pushability of the guidewire through substantial vascular lengths and in order to provide adequate torque transmission along the guidewire. At the same time, proximal wire segment 10 of the composite guidewire still requires some flexibility, in order to permit the guidewire to navigate through highly tortuous anatomy. Thus, in one preferred form of the present invention, proximal wire segment 10 comprises stainless steel. Furthermore, distal wire segment 15 generally requires higher elasticity and lower stiffness, in order to provide sufficient flexibility to navigate through highly tortuous anatomy. At the same time, distal wire segment 15 of the composite guidewire still requires some stiffness, in order to maintain the torque transmission requirements of the guidewire and to provide sufficient support for stent delivery. Thus, in one preferred form of the present invention, distal wire segment 15 comprises Nitinol, or another "super-elastic" or "pseudo-elastic" or "linear elastic" material.

Joint 20 is formed so as to preserve the integrity of the guidewire. In other words, joint 20 provides adequate (i) tensile strength, (ii) torque strength, (iii) bending moment performance, and (iv) failure mode characteristics, among other things. To this end, joint 20 is formed by complementary flat planar bonding faces, suitable for overlapping bonding, which are created at the joint ends of the two wire segments which are to be joined. The complementary flat planar bonding faces are of sufficient surface area to provide, once they are bonded in overlapping fashion, the required tensile strength and torque strength for the guidewire.

As will hereinafter be discussed in further detail, in one preferred form of the invention, each of the complementary flat planar bonding faces comprises a single surface. In another preferred form the invention, each of the complementary flat planar bonding faces comprises a plurality of surfaces.

As will also hereinafter be discussed in further detail, gradual transitions may be added along the lengths of the wire segments so as to provide the required bending moment performance, e.g., the wire segments may be configured so as to provide a monotonic transition of the bending moment along the length of the composite guidewire.

Furthermore, and as will hereinafter be discussed in further detail, the joint of the composite guidewire may be configured so as to provide the desired failure mode characteristics.

More particularly, in one preferred form of the invention, and looking now at FIGS. 1 and 2, joint 20 is formed by (i) a flat planar bonding face 25 formed at the distal end of proximal wire segment 10, and (ii) a complementary flat planar bonding face 30 formed at the proximal end of distal wire segment 15. Flat planar bonding face 25 is positioned against flat planar bonding face 30, with surface 35 of proximal wire segment 10 engaging surface 40 of distal wire segment 15, and with surface 45 of proximal wire segment 10 engaging surface 50 of distal wire segment 15, and then the two wire segments are bonded together in overlapping fashion at the joint line so as to form composite guidewire 5. In essence, proximal wire segment 10 comprises a tongue 55 which includes the flat planar bonding face 25, and distal wire segment 15 comprises a tongue 60 which includes the complementary flat planar bonding face 30.

Thus, in this form of the invention, the complementary flat planar bonding faces 25, 30 each comprise a single surface.

The strength of joint 20 is provided by the bonded overlapping flat planar bonding faces 25, 30. More particularly, bonded overlapping flat planar bonding faces 25, 30:

(i) provide a length along which forces may be distributed—in principle, the lengths of flat planar bonding faces 25, 30 correlate directly to the strength of the joint, with longer flat planar faces yielding higher joint strengths; at some length, the strength of the joint can actually exceed the material strength of one or both of the parent wire segments so that, when the joint is loaded, a parent wire segment 10, 15 will break before the joint 20 will break—this principle holds true even when using a bonding material (e.g., an adhesive or solder) that has a lower material strength than the material strength of one or both of the parent wire segments; and (ii) provide excellent torque transmission—unlike tubular connectors, where rotational slippage is possible when torque loads are high, the bonded overlapping flat planar bonding faces 25, 30 do not allow for torque loss to occur (of course, when very high torsional loads are applied to the joint, torque loss may be experienced across the bond as plastic deformation is imparted onto the bonded overlapping flat planar bonding faces 25, 30, i.e., as the bonded overlapping flat planar bonding faces are twisted).

Among other things, it has been found that both tensile strength and torsional strength are a function of the length of the bond established between the proximal wire segment 10 and the distal wire segment 15, i.e., it has been found that both tensile strength and torsional strength are a function of the length of the overlapping flat planar bonding faces 25, 30. In particular, it has been found that by making the length of the overlapping flat planar bonding faces 25, 30 between about 5 and about 50 times the cross-sectional diameter of the composite guidewire, a joint 20 can be formed which has excellent tensile strength and torque strength, while still providing excellent bending moment performance, and failure mode characteristics, among other things.

Furthermore, it should also be appreciated that by forming joint 20 by bonding together, in overlapping fashion, the two complementary flat planar bonding faces 25, 30, where those complementary flat planar bonding faces extend parallel to the longitudinal axis of the composite guidewire for a substantial length, stress concentration at the joint is dramatically reduced vis-à-vis a conventional joint construction where two wires are joined in an end-to-end fashion.

The flat planear bonding face 25 formed in proximal wire segment 10, and/or the flat planar bonding face 30 formed in distal wire segment 15, are preferably formed by grinding or machining. It should be appreciated that when complementary flat planar bonding faces 25, 30 are formed by grinding or machining, it is important that (i) enough of the original wire segment be removed so as to create a flat planar bonding face which is large enough to provide adequate contact and holding power, but (ii) enough of the original wire segment be retained so as to maintain the integrity of the wire segment.

Flat planar bonding faces 25, 30 may be formed on the half-round (i.e., flat planar bonding faces 25, 30 may be positioned on the diameter, in the manner shown in FIGS. 1 and 2), but they are not necessarily so formed. Among other things, flat planar bonding faces 25, 30 may be formed, complementarily, offset from the line crossing the center of the wire segment, i.e., offset from the diameter line. In other words, flat planar bonding faces 25, 30 may be positioned on the diameter, in the manner shown in FIGS. 1 and 2, so that each tongue 55, 60 has a half-circle cross-section; or flat planar bonding faces 25, 30 may be positioned off the diameter, in the manner shown in FIG. 3, so that each tongue 55, 60 has more or less than a half-circle cross-section. Stated another way, the two tongues 55, 60 can be equal in cross-section, in the manner shown in FIGS. 1 and 2; or the two tongues 55, 60 may complementarily vary in cross-section, in the manner shown in FIG. 3.

For one ideal case, flat planar bonding faces 25, 30 are formed in proximal wire segment 10 and distal wire segment 15, respectively, so that the break-loads of each wire segment 10, 15 (i.e., the break-loads of each tongue 55, 60) are equal. In other words, the relative positions of flat planar bonding faces 25, 30 are set (in a radial sense) by taking into account the ultimate tensile strengths (UTS) of the materials forming each of the wire segments 10, 15, so that each wire segment (i.e., each tongue 55, 60) has an equal break load.

For example:

Break load(proximal wire segment 10)=Break load (distal wire segment 15)

and $A*UTS$(proximal wire segment 10)=$A*UTS$(distal wire segment 15)

where A=the cross-sectional area of the wire segment. See, for example, FIGS. 3-5, where the UTS for proximal wire segment 10 is greater than the UTS for distal proximal wire segment 15, so that flat planar bonding face 25 is set to provide a thinner tongue 55 and flat planar bonding face 30 is set to provide a thicker tongue 60. Providing tongues of different relative thicknesses allows wire segments of different material strengths to break at the same time.

Thus, for example, where composite guidewire 5 comprises a proximal wire segment 10 made of stainless steel and a distal wire segment 15 made of Nitinol, inasmuch as stainless steel has a UTS which is 1.5 times the UTS of Nitinol, tongue 55 of proximal wire segment 10 might have a smaller cross-section than tongue 60 of distal wire segment 15.

In the constructions shown in FIGS. 1-3, the complementary flat planar bonding faces 25, 30 each comprise a single surface. However, it is also possible for each of the complementary flat planar bonding faces 25, 30 to comprise a plurality of surfaces.

Figures 6, 7, 8:
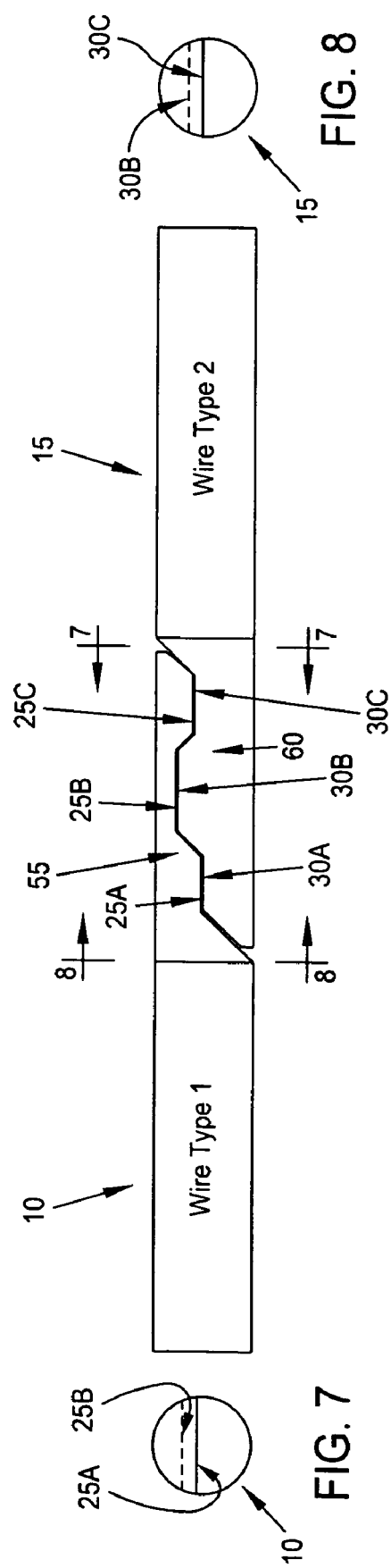
FIG. 6 is a view like that of FIG. 3, but showing another joint construction.
FIG. 7 is a sectional view taken along line 7-7 of FIG. 6.
FIG. 8 is a sectional view taken along line 8-8 of FIG. 6.

More particularly, it is also possible for flat planar bonding face 25 and complementary flat planar bonding face 30 to each comprise a plurality of surfaces, which may or may not lie co-planar with one another. By way of example but not limitation, in FIGS. 6-8, flat planar bonding face 25 comprises flat planar surfaces 25A, 25B and 25C, and complementary flat planar bonding face 30 comprises flat planar surfaces 30A, 30B and 30C; and in FIGS. 9-11, flat planar bonding face 25 comprises flat planar surfaces 25A and 25B, and complementary flat planar bonding face 30 comprises flat planar surfaces 30A and 30B.

Significantly, by forming both flat planar bonding face 25 and complementary flat planar bonding face 30 out of a plurality of corresponding flat planar surfaces, and by varying the radial positions of the various flat planear surfaces, tongues 55 and 60 can be given an interlocking character which can further assist stabilization of joint 20.

Again, where flat planar bonding face 25 and complementary flat planar bonding face 30 are formed out of a plurality of corresponding flat planar surfaces, it has been found that, by making the collective length of the bonded overlapping flat planar bonding faces 25, 30 between about 5 and about 50 times the cross-sectional diameter of the composite guidewire, a joint 20 can be formed which has excellent tensile strength and torque strength, while still providing excellent bending moment performance, and failure mode characteristics, among other things.

Furthermore, surfaces 35, 40, 45 and 50 may or may not extend perpendicular to the longitudinal axis of composite guidewire 5. Thus, for example, in FIGS. 1-3, surfaces 35, 40, 45 and 50 all extend perpendicular to the longitudinal axis of composite guidewire 5, whereas in FIGS. 12-14, surfaces 35A, 40A, 45A and 50A all extend at an acute angle to the longitudinal axis of composite guidewire 5. Furthermore, where flat planar bonding face 25 comprises a plurality of flat planar surfaces, and flat planar bonding face 30 comprises a plurality of flat planar surfaces, such as is shown in FIGS. 6-8 and 9-11, surfaces 35, 40, 45 and 50 may extend at an acute angle to the longitudinal axis of the composite guidewire.

Figure 15:
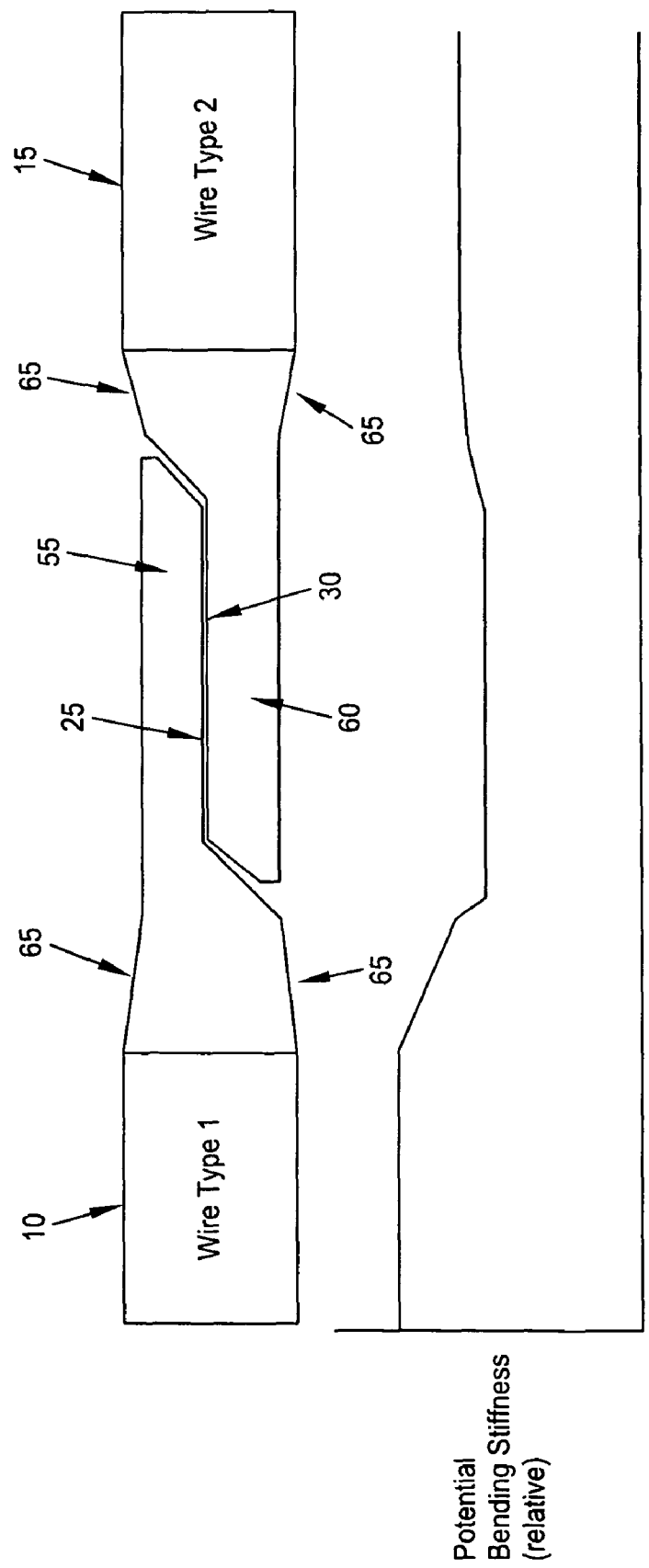
FIG. 15 is a view like that of FIG. 12, but showing another joint construction, and showing the potential bending stiffness along the relevant portion of that guidewire.
Figure 16:
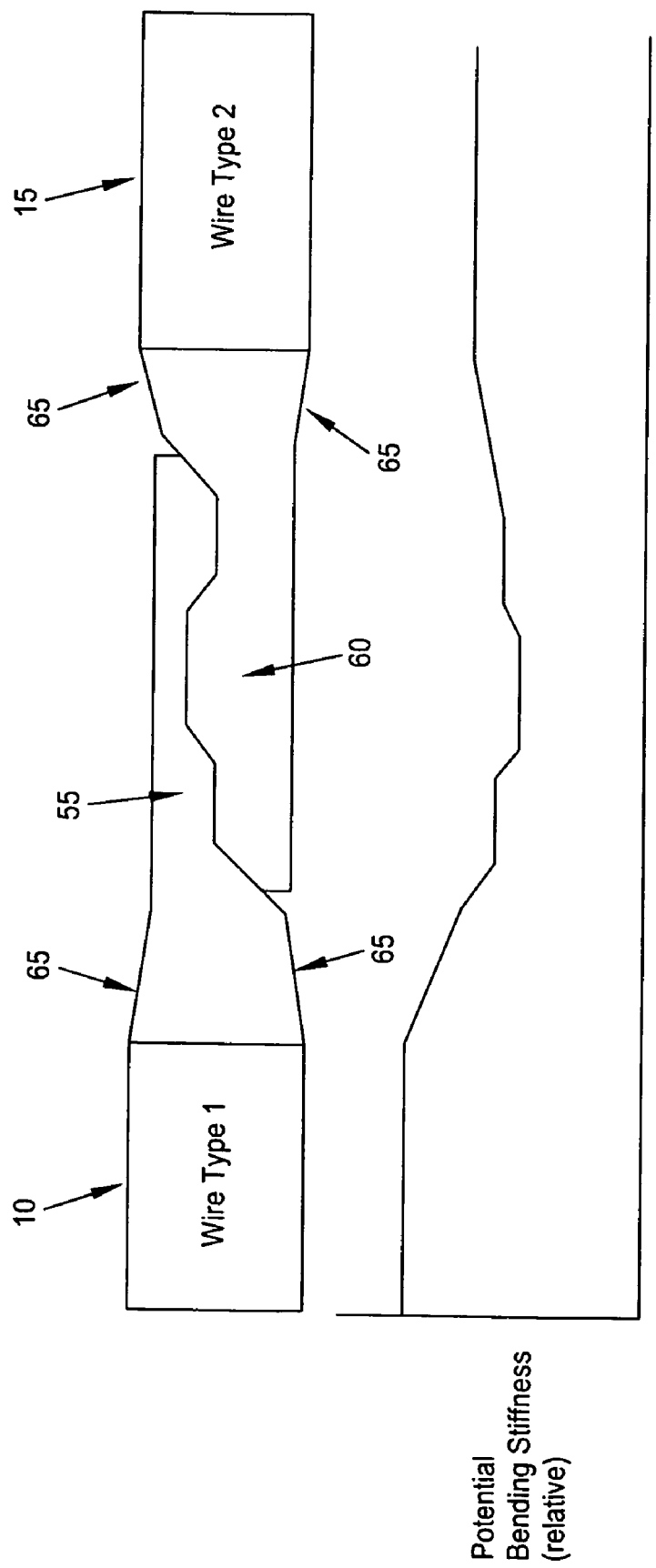
FIG. 16 is a view like that of FIG. 15, but showing another joint construction, and showing the potential bending stiffness along the relevant portion of that guidewire.

If desired, the proximal wire segment 10 and the distal wire segment 15 may be reduced in diameter before joint 20, i.e., before flat planar bonding faces 25 and 30 begin. This construction may be used to reduce the bending moment experienced at the joint by distributing the bend across a longer length, thereby distributing the focus of the bending moment across a larger zone and beyond that of the bonded overlapping complementary flat planar bonding faces 25, 30. See, for example, FIGS. 15 and 16, where the outer surfaces of the proximal wire segment 10 and distal wire segment 15 are tapered as shown at 65.

As noted above, the two complementary flat planar bonding faces 25, 30 are aligned with one another in an overlapping fashion, and then the complementary flat planar bonding faces are bonded together. Such bonding may be effected with adhesives; and/or welding; and/or crimping; and/or overlying metal and/or polymer sleeves (either braided or solid); etc.

Figure 17:
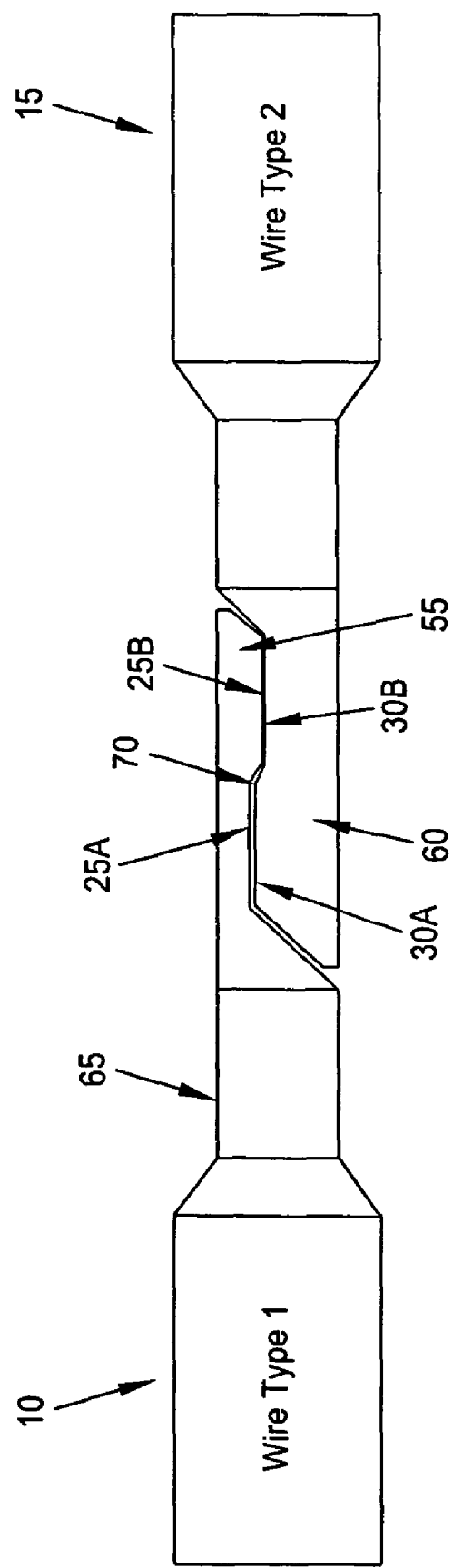
FIG. 17 is a side view of a composite guidewire formed in accordance with the present invention, wherein the guidewire utilizes a joint comprising an adhesive material applied to the complementary flat planar bonding faces of the wire segments.
Figure 18:
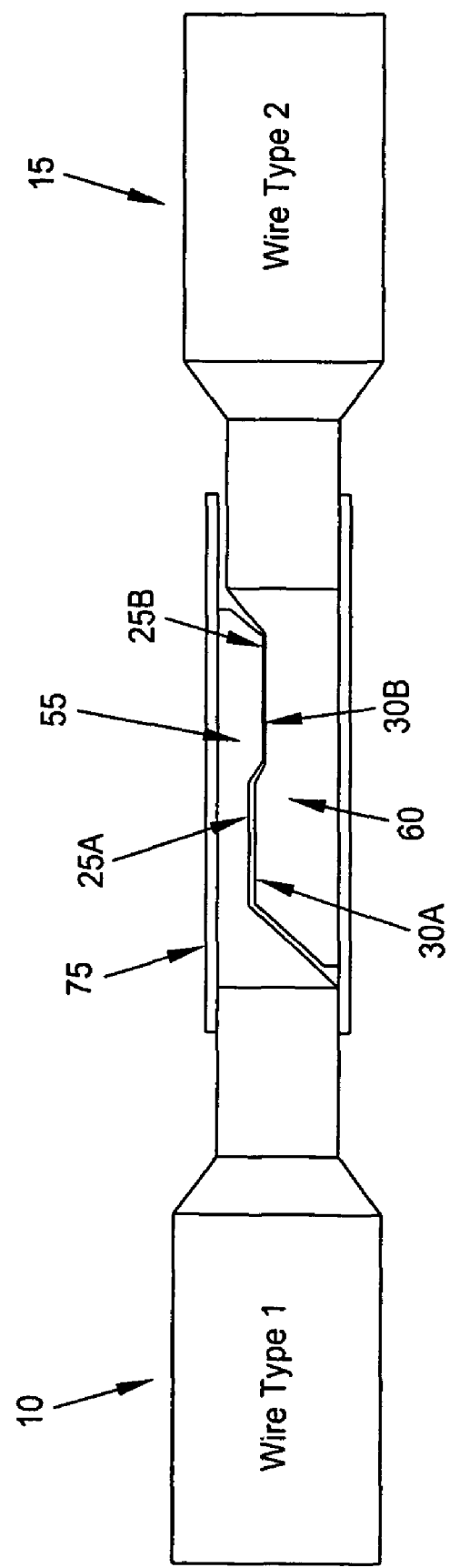
FIG. 18 is a side view like that of FIG. 17, but omitting the adhesive material and instead showing a joint surrounded by a polymer shrink sleeve.
Figure 19:
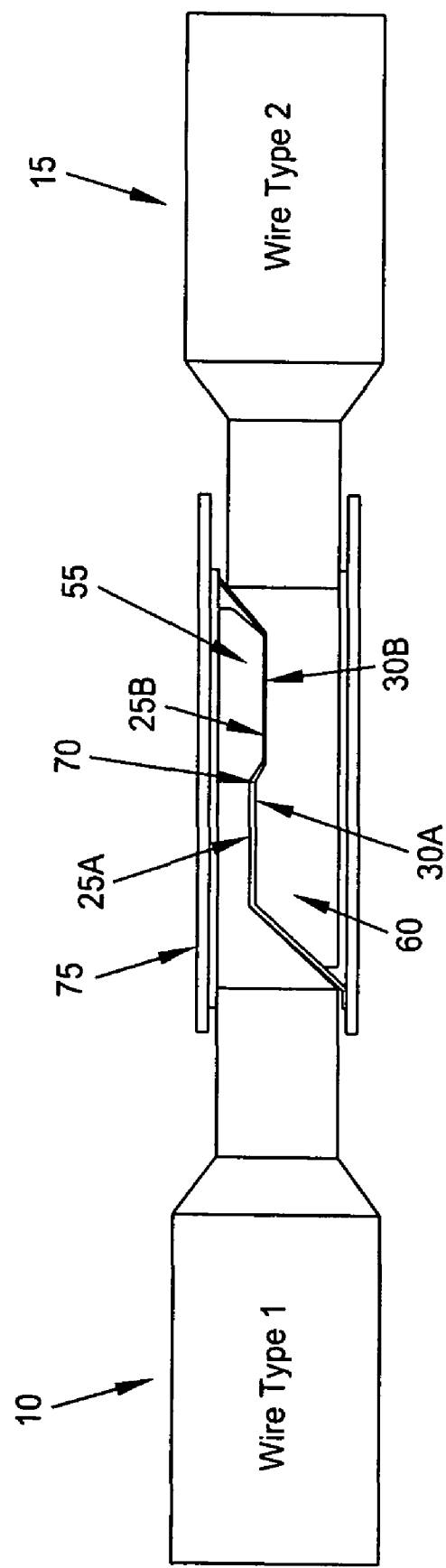
FIG. 19 is a side view like that of FIGS. 17 and 18, wherein the joint comprises both an adhesive material applied to the complementary flat planar bonding faces of the wire segments and a polymer shrink sleeve surrounding the joint.
Figure 20:
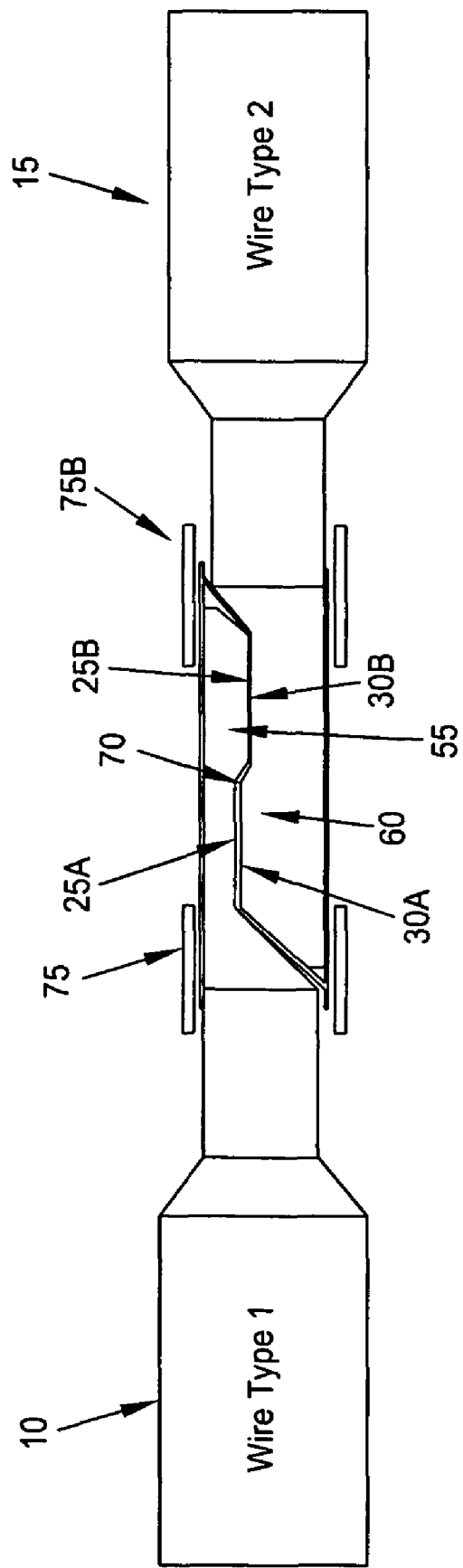
FIG. 20 is a side view like that of FIG. 17, but showing a joint utilizing a pair of polymer shrink sleeves.
Figure 21:
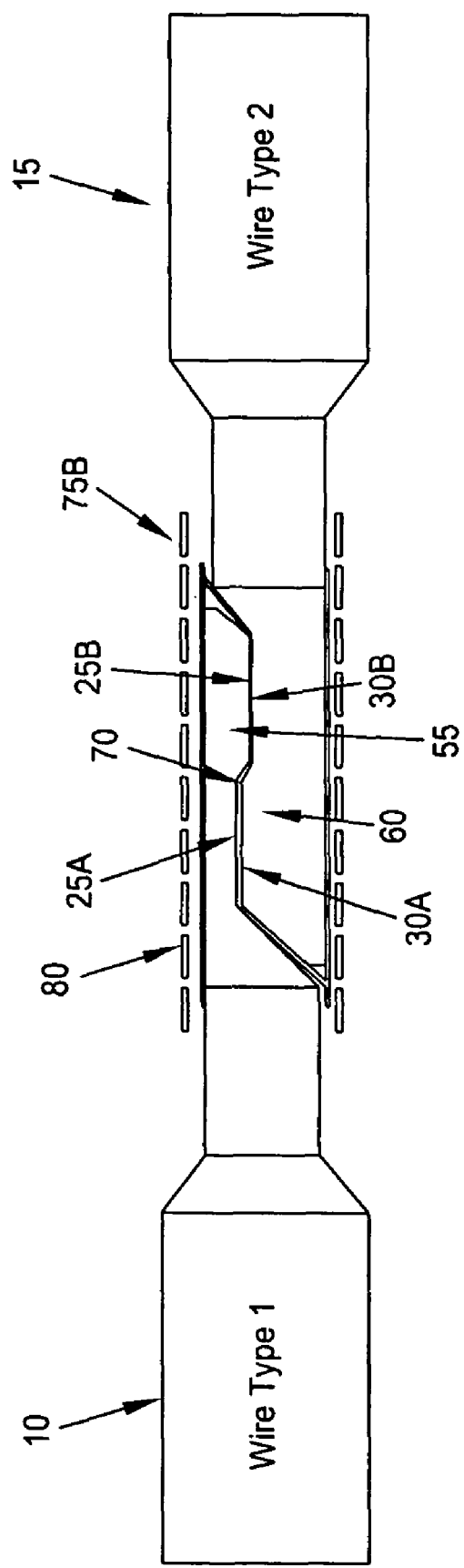
FIG. 21 is a side view like that of FIG. 17, but showing a joint utilizing a metal coil.
Figure 22:
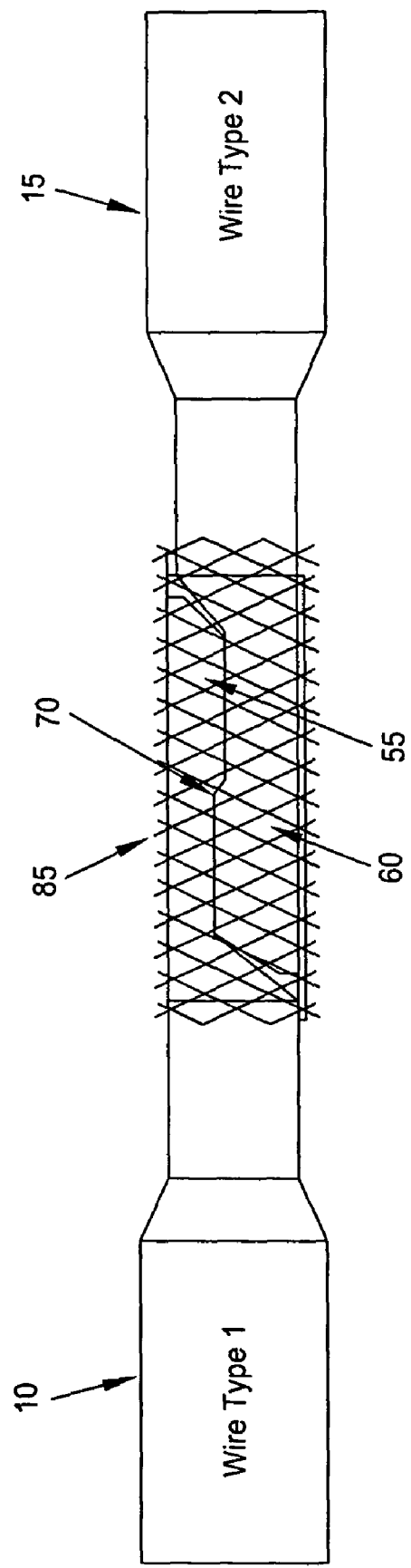
FIG. 22 is a side view like that of FIG. 21 but showing a joint utilizing a braided member.

By way of example but not limitation, tongues 55, 60 of joint 20 may be bonded together by using:
(i) intermediate means, including:
  (a) adhesives (e.g., epoxies, urethane acrylics, cyanoacrylates, etc.);
  (b) metallurgical bonding materials (e.g., braze, including AuGe; solder, including AuSn and SnAg, etc., with or without various fluxes, etching solutions, or plating methods to facilitate the metallurgical bond;
  (c) welds (including filler materials as necessary to diminish imbrittlement); etc;
  see, for example, FIG. 17, where epoxy, adhesive, solder, weld 70 is used to bond, in an overlapping fashion, complementary flat planar surfaces 25A, 25B to 30A, 30B, respectively; and
(ii) mechanical means, including:
  (a) crimping;
  (b) shrink sleeves; see, for example, FIG. 18, where a polymer or metal shrink sleeve 75 is used to bond, in an overlapping fashion, complementary flat planar surfaces 25A, 25B to 30A, 30B, respectively; FIG. 19, where epoxy adhesive 70 and polymer or metal shrink sleeve 75 are both used to bond, in an overlapping fashion, complementary flat planar surfaces 25A, 25B to 30A, 30B, respectively; FIG. 20, where epoxy adhesive 70 and a pair of separated polymer or metal shrink sleeves 75A, 75B are all used to bond, in an overlapping fashion, complementary flat planar surfaces 25A, 25B to 30A, 30B, respectively; FIG. 21, where epoxy adhesive 70 and a polymer or metal coil 80 are both used to bond, in an overlapping fashion, complementary flat planar surfaces 25A, 25B to 30A, 30B, respectively; FIG. 22, where epoxy adhesive 70 and a polymer or metal braided member 85 are both used to bond, in an overlapping fashion, complementary flat planar surfaces 25A, 25B to 30A, 30B, respectively; where the polymers may comprise any suitable biocompatible polymer including, but not limited to, PET, PTFE, FEP, polyimide, polyurethane, polyethylene, poly propylene, Pebax, etc.; and where the metals may comprise any suitable biocompatible metal including, but not limited to, stainless steel, Nitinol, etc;
  (c) coils and/or braids, etc.; where the coils and/or braids may be made from polymers or metals, and where the polymers may comprise any suitable biocompatible polymer including, but not limited to, PET, PTFE, FEP, polyimide, polyurethane, polyethylene, poly propylene, Pebax, etc.; and where the metals may comprise any suitable biocompatible metal including, but not limited to, stainless steel, Nitinol, etc;

Where mechanical means are used to secure joint 20, and where those mechanical means comprise sleeves, coils and/or braided members, etc., such sleeves, coils and/or braided members can further act as protective coverings to cover over any surface roughness from the adhesives, solder spots, etc. or from the edges of the wire segments. This can be significant, since it can help reduce the possibility of the guidewire binding with another device, e.g., a catheter. Furthermore, these protective coverings also may serve to hold in place the ends of the wire segments (i.e., tongues 55, 60) when a bending moment occurs to the bond, so as to protect against any peeling effect at the ends of wire segments 10, 15. In addition, to the extent that the protective coverings comprise stronger (e.g., more metallic) coverings, these protective coverings can also serve as a tether to hold the two wire segments together in the event that bond breakage occurs.

Figure 23:
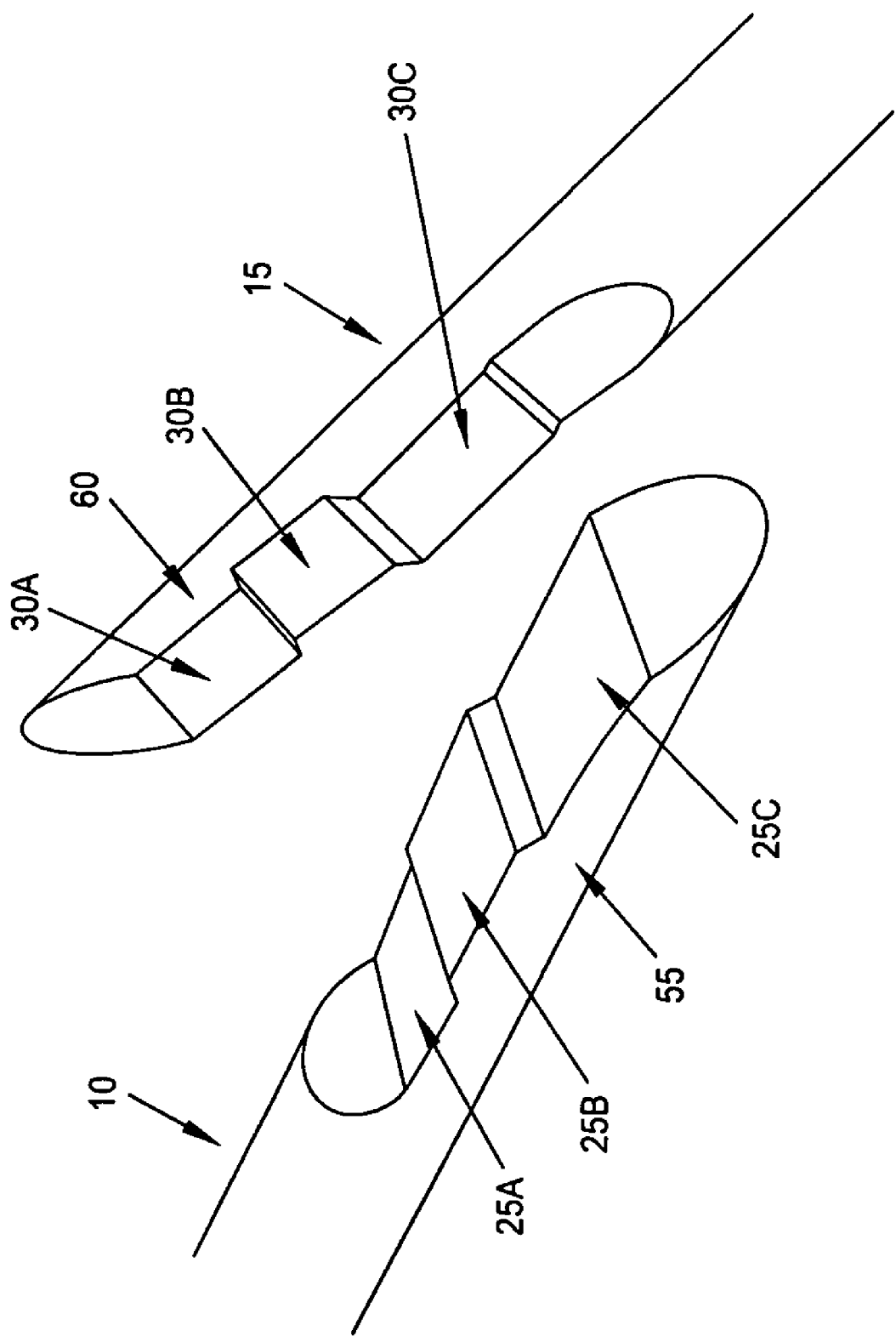
FIG. 23 is a schematic view showing another possible joint construction for the composite guidewire of the present invention.
Figure 24:
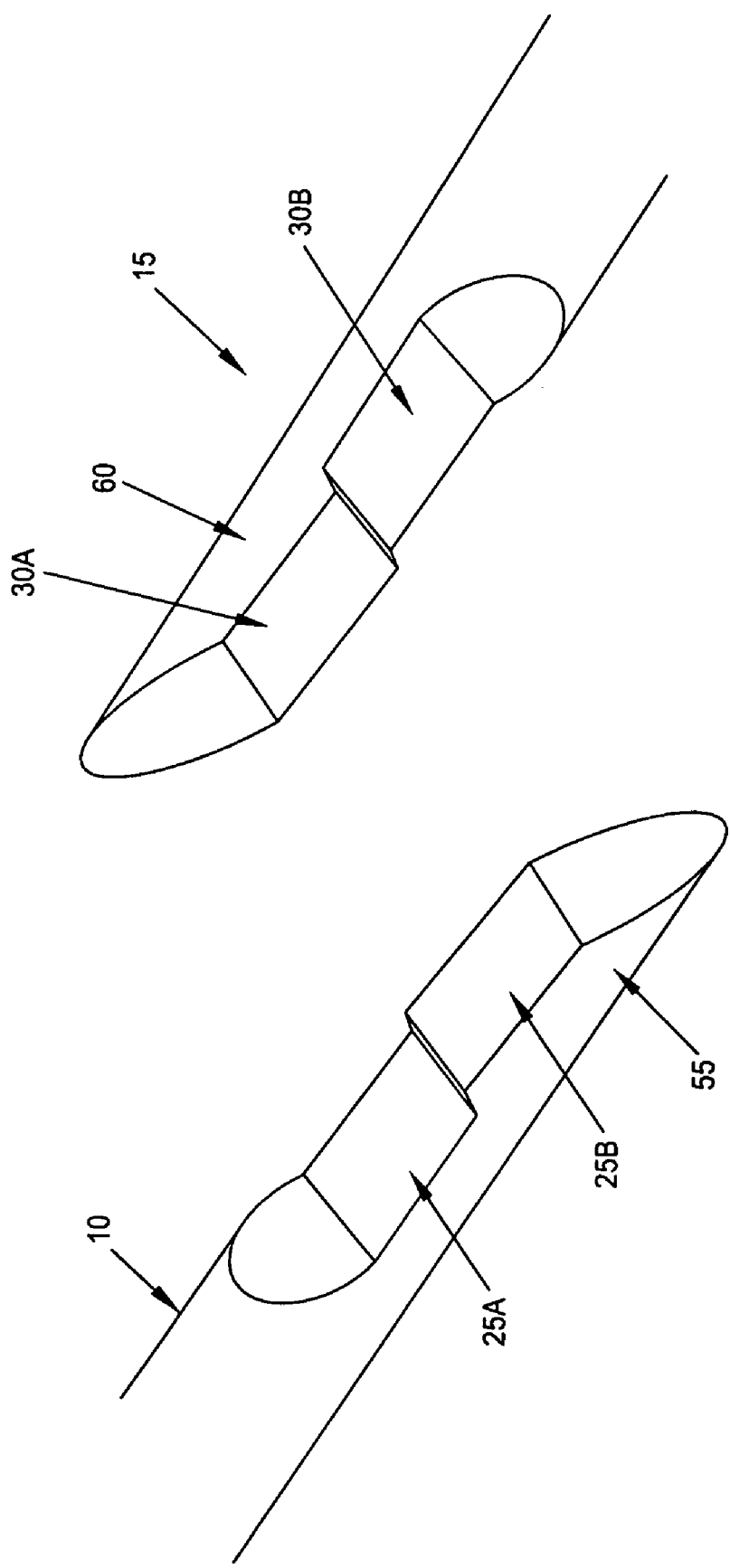
FIG. 24 is a schematic view showing another possible joint construction for the composite guidewire of the present invention.
Figure 26:
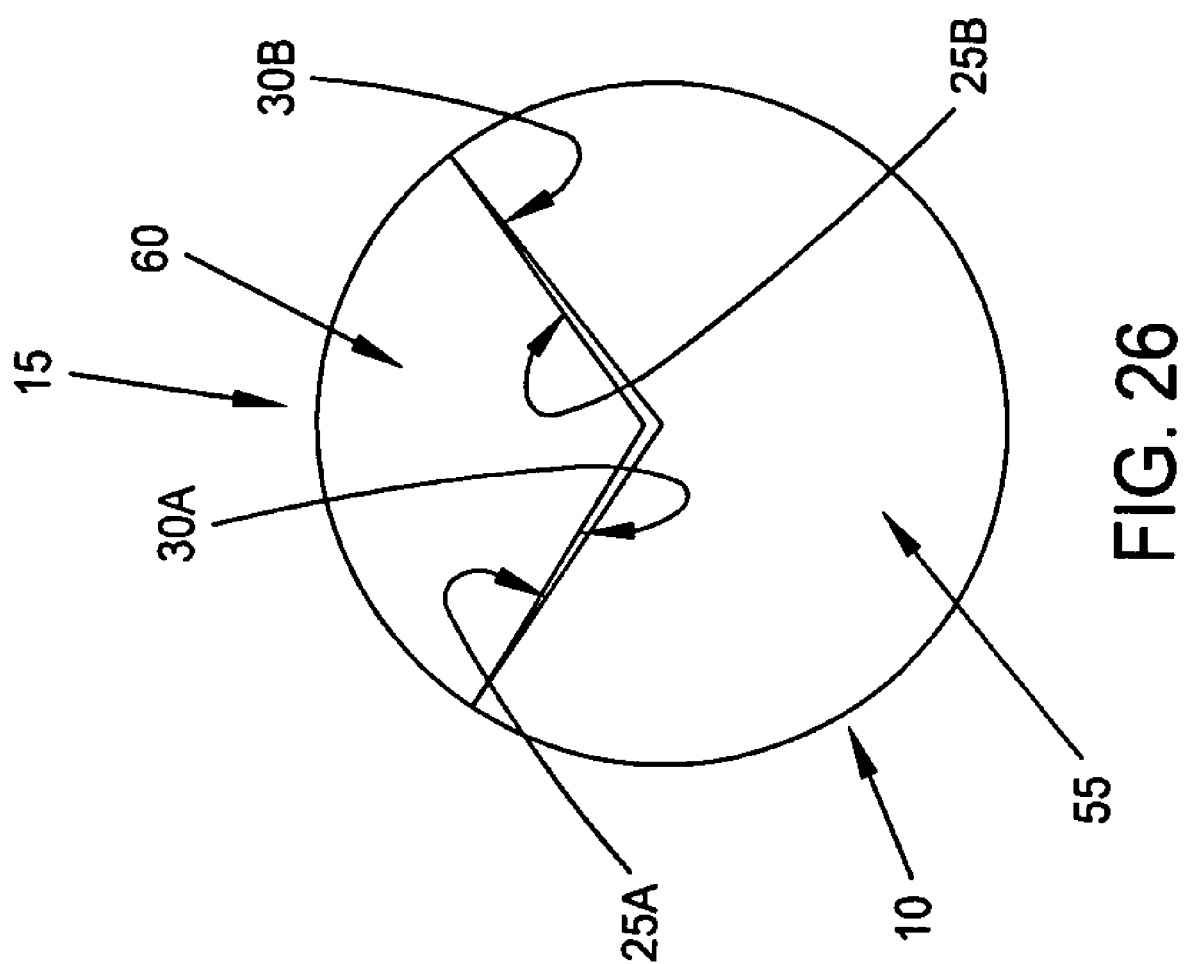
FIG. 26 is a sectional view taken through the assembled composite guidewire of FIG. 25.
Figure 27:
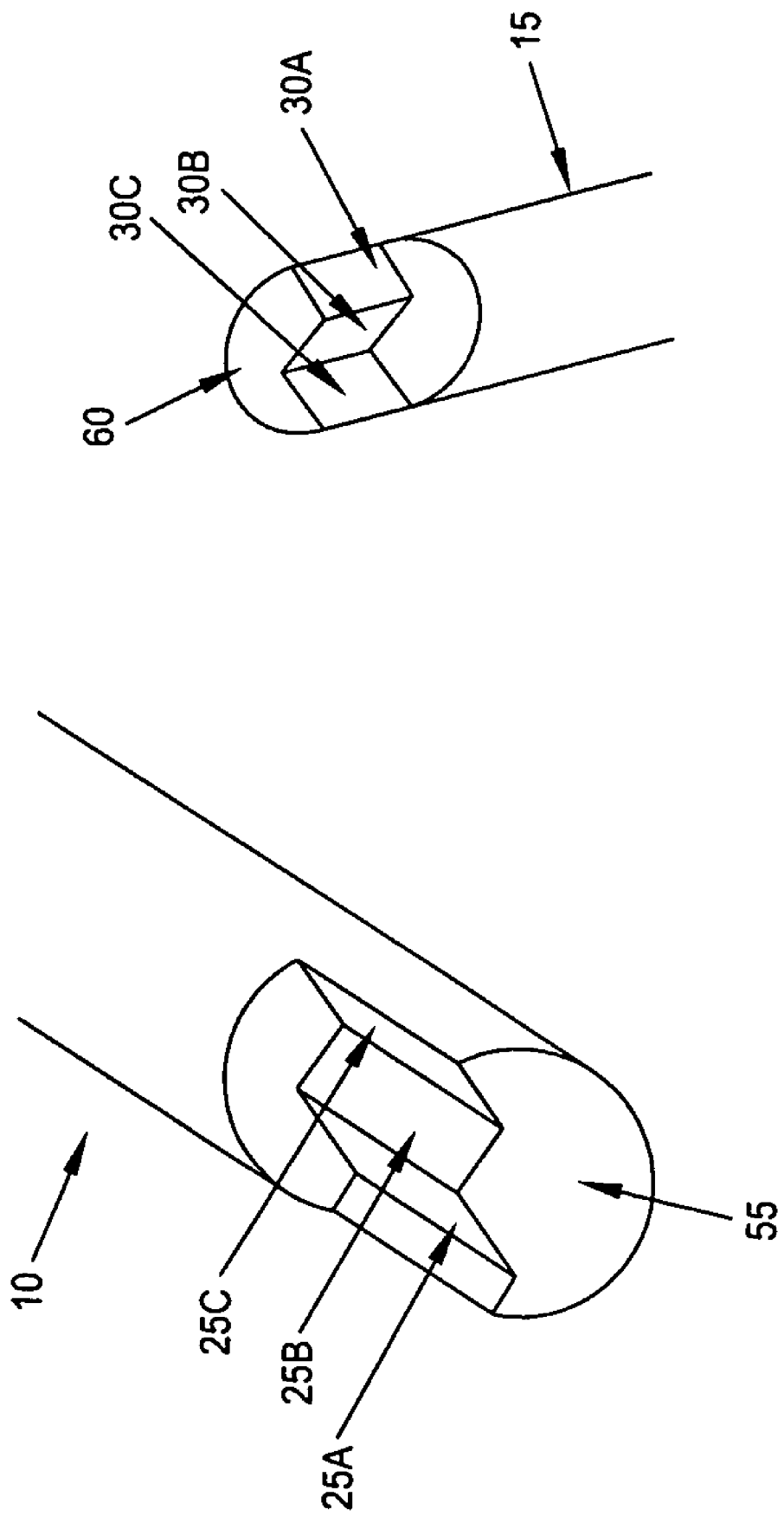
FIG. 27 is a schematic view showing another possible joint construction for the composite guidewire of the present invention.
Figure 28:
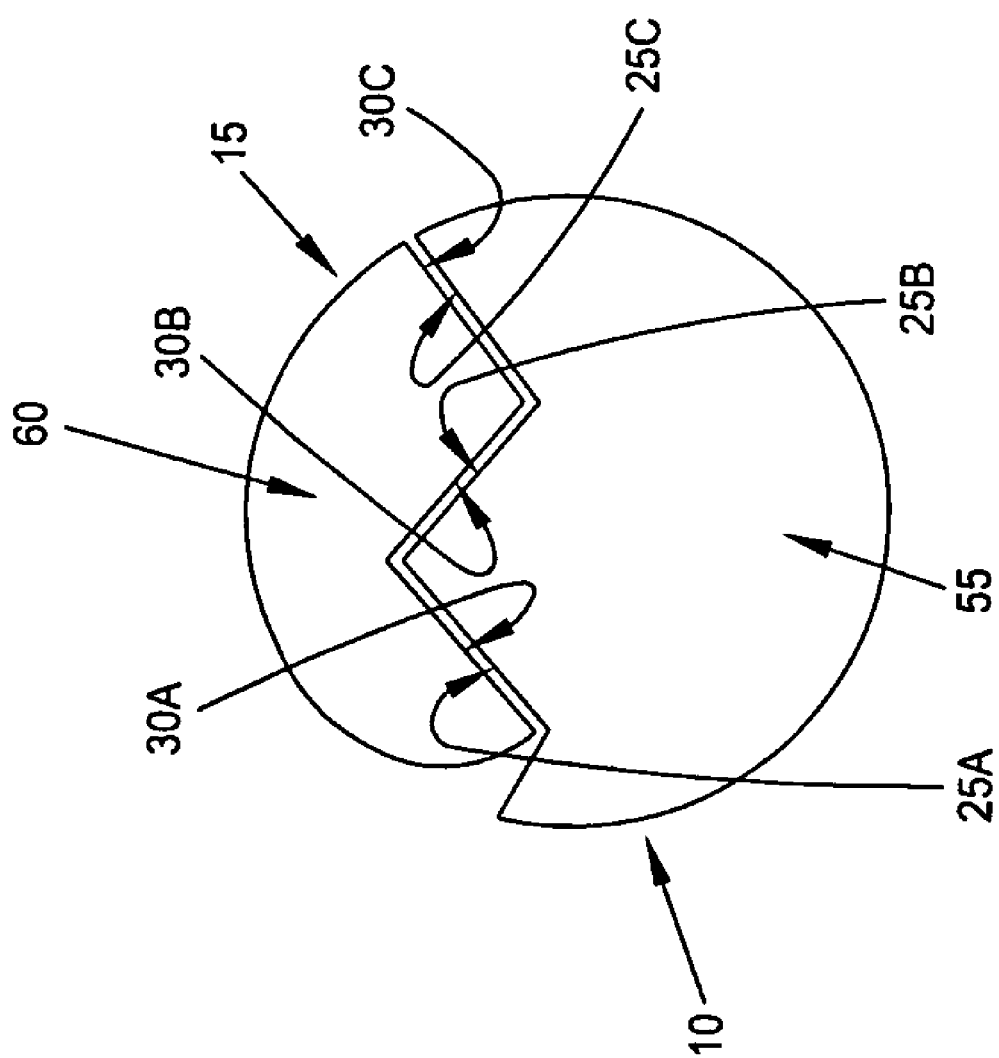
FIG. 28 is a sectional view taken through the assembled composite guidewire of FIG. 27.

It is also possible to provide other configurations for the complementary flat planar bonding faces 25, 30. Thus, for example, FIG. 23 shows one exemplary joint configuration in which tongue 55 comprises a set of flat planar surfaces 25A, 25B, 25C and tongue 60 comprises a complementary set of flat planar surfaces 30A, 30B, 30C; FIG. 24 shows another exemplary joint configuration in which tongue 55 comprises a set of flat planar surfaces 25A, 25B and tongue 60 comprises a complementary set of flat planar surfaces 30A, 30B; FIGS. 25 and 26 show another exemplary joint configuration in which tongue 55 comprises a set of flat planar surfaces 25A, 25B and tongue 60 comprises a complementary set of flat planar surfaces 30A, 30B; and FIGS. 27 and 28 show another exemplary joint configuration in which tongue 55 comprises a set of flat planar surfaces 25A, 25B, 25C and tongue 60 comprises a complementary set of flat planar surfaces 30A, 30B, 30C.

Figure 29:
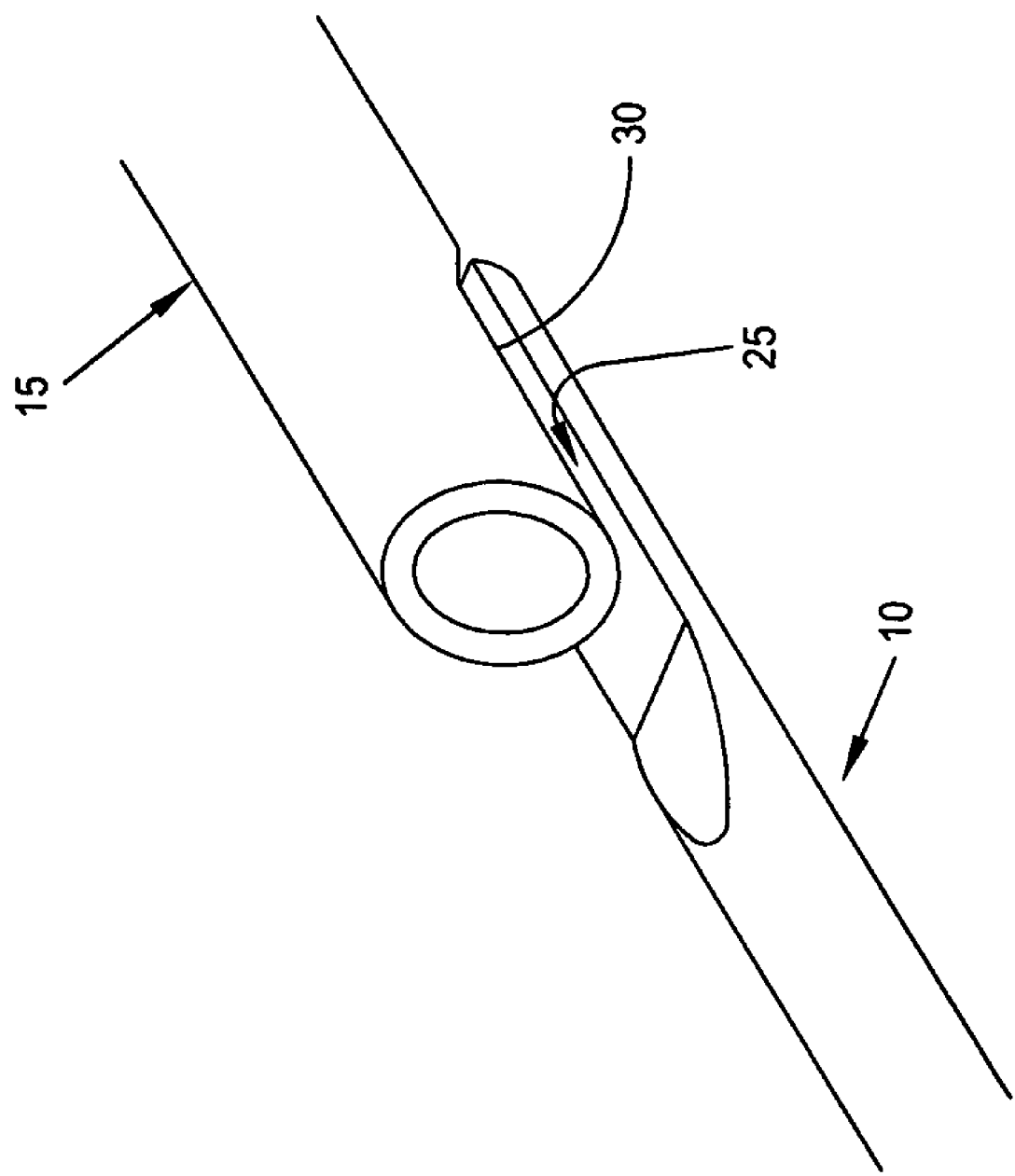
FIG. 29 is a schematic view showing another possible joint construction for the composite guidewire of the present invention.
Figure 30:
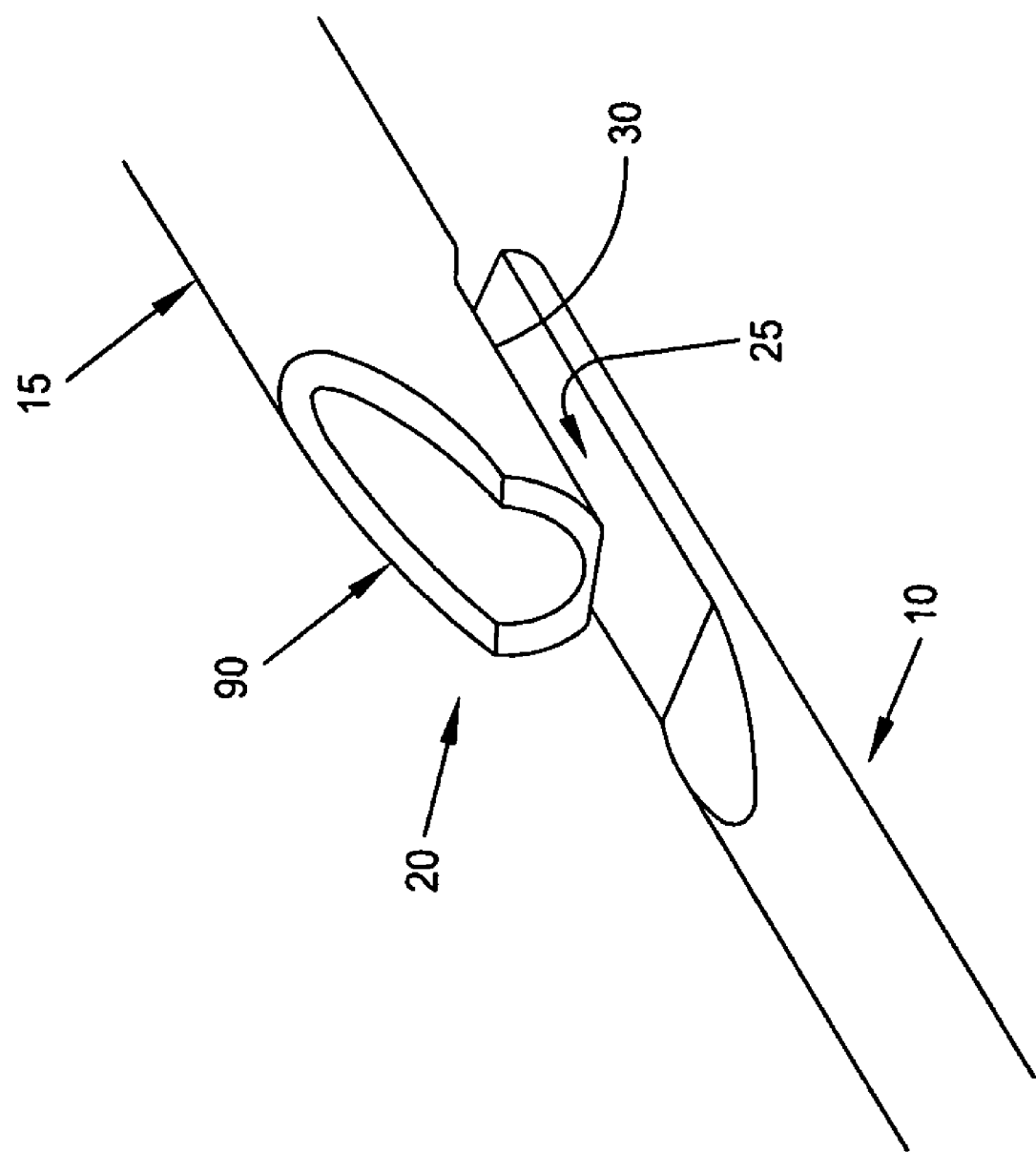
FIG. 30 is a schematic view showing another possible joint construction for the composite guidewire of the present invention.

It is also possible to utilize hollow bodies for proximal wire segment 10 and/or distal wire segment 15. In this case, appropriate complementary flat planar bonding faces 25, 30 are provided on the hollow body, see, for example, FIG. 29, where flat planar bonding face 25 is formed on a solid proximal wire segment 10, and a counterpart flat planar bonding face 30 is formed on a hollow body distal wire segment 15; and FIG. 30, where flat planar bonding face 25 is formed on a solid proximal wire segment 10, and a counterpart flat planar bonding face 30 is formed on a hollow body distal wire segment 15, and further wherein hollow body distal wire segment 15 is cut back at 90 so as to reduce the side profile of joint 20. Where composite guidewire 5 utilizes a hollow body (i.e., a tube), it may be beneficial to blend the stiffnesses of the two adjoining segment materials. This can be accomplished by annealing the proximal joining end of the hollow body so as to reduce the stiffness of the hollow body. To this end, the proximal end of the hollow body may be annealed so as to provide an increased austenitic finish temperature.

In the preceding discussion, the present invention is discussed in the context of a composite guidewire 5 formed out of two wire segments (i.e., proximal wire segment 10 and distal wire segment 15) joined together at a joint 20. However, it should be appreciated that the composite guidewire 5 may comprise more than two wire segments, in which case the composite guidewire will include more than one joint 20. By way of example, composite guidewire 5 may comprise three wire segments and two joints; or composite guidewire 5 may comprise four wire segments and three joints; etc.

Composite guidewire 5 of the present invention is preferably formed so as to have a diameter of between about 0.010 inches and about 0.038 inches. However, it should be appreciated that composite guidewire 5 may also be formed so as to have other diameters as well.

Furthermore, the present invention could be embodied in devices other than coronary guidewires. By way of example but not limitation, the present invention could be embodied in other types of guidewires, or the present invention could be embodied in other wire-based devices including, but not limited to, snares; retrievers and graspers; embolic protection devices (e.g., filters); detachable devices that position embolic materials and implantable filters; biopsy devices; devices that deliver energy such as ultrasound, electric current, and radiofrequency; etc. Depending on the application, the composite wire may comprise more than two wire segments, the most flexible wire segment may be located at other than the distal end of the composite wire, etc.

MODIFICATIONS OF THE PREFERRED EMBODIMENTS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A composite guidewire comprising:
   a proximal wire segment having a proximal end, a distal end, and a longitudinal axis extending between the proximal end and the distal end, the distal end of said proximal wire segment comprising a first tongue having a first flat planar bonding face which extends parallel to the longitudinal axis, said proximal wire segment having a first elasticity and being formed out of a first material having a first ultimate tensile strength;
   a distal wire segment having a proximal end, a distal end, and a longitudinal axis extending between the proximal end and the distal end, the proximal end of said distal wire segment comprising a second tongue having a second flat planar bonding face which extends parallel to the longitudinal axis, said distal wire segment having a second elasticity and being formed out of a second material having a second ultimate tensile strength, wherein the second material is different than the first material, and further wherein the second ultimate tensile strength is different than the first ultimate tensile strength;
   wherein the second flat planar bonding face of said second tongue of said distal wire segment is formed complementary to the first flat planar bonding face of said first tongue of said proximal wire segment;
   wherein said proximal wire segment is joined to said distal wire segment by bonding the first flat planar bonding face of said first tongue of said proximal wire segment to the complementary second flat planar bonding face of said second tongue of said distal wire segment in an overlapping manner;
   wherein said first tongue and said second tongue have complementary but dissimilar cross-sections;
   and further wherein the cross-sections of said first and second tongues are set in relation to each other such that a break load of said first tongue is equal to a break load of said second tongue throughout lengths of the bonding faces of said tongues.

2. A composite guidewire according to claim 1 wherein said proximal wire segment has a cross-section which comprises an arc, said distal wire segment has a cross-section which comprises an arc, and further wherein the composite guidewire has a round cross-section at a point where said proximal wire segment is joined to said distal wire segment.

3. A composite guidewire according to claim 1 wherein said first tongue and said second tongue are configured so as to interlock with one another.

4. A composite guidewire according to claim 1 wherein the composite guidewire has a round cross-section where said proximal wire segment is joined to said distal wire segment.

5. A composite guidewire according to claim 1 wherein the first elasticity of said proximal wire segment and the second elasticity of said distal wire segment are different from one another.

6. A composite guidewire according to claim 1 wherein the second elasticity of said distal wire segment is higher than the first elasticity of said proximal wire segment.

7. A composite guidewire according to claim 1 wherein the first elasticity of said proximal wire segment is higher than the second elasticity of said distal wire segment.

8. A composite guidewire according to claim 1 wherein said proximal wire segment comprises stainless steel.

9. A composite guidewire according to claim 1 wherein said distal wire segment comprises Nitinol.

10. A composite guidewire according to claim 1 wherein the length of the bonded, overlapping first and second flat planar bonding faces is between about 5 and about 50 times the cross-sectional diameter of the composite guidewire.

11. A composite guidewire according to claim 1 wherein said proximal wire segment is joined to said distal wire segment using at least one selected from the group consisting of: an adhesive, a metallurgical bonding material, and a weld.

12. A composite guidewire according to claim 11 wherein the adhesive is selected from the group consisting of: epoxies, urethane acrylics, and cyano-acrylates.

13. A composite guidewire according to claim 11 wherein the metallurgical bonding material is selected from the group consisting of: braze and solder.

14. A composite guidewire according to claim 1 wherein said proximal wire segment is joined to said distal wire segment by mechanical means.

15. A composite guidewire according to claim 14 wherein the mechanical means comprises at least one selected from the group consisting of: crimping, shrink sleeves, coils and braids.

16. A method for forming a composite guidewire, the method comprising the steps of:
   providing a proximal wire segment having a proximal end, a distal end, and a longitudinal axis extending between the proximal end and the distal end, the distal end of the proximal wire segment comprising a first tongue having a first flat planar bonding face which extends parallel to the longitudinal axis, the proximal wire segment having a first elasticity and being formed out of a first material having a first ultimate tensile strength;
   providing a distal wire segment having a proximal end, a distal end, and a longitudinal axis extending between the proximal end and the distal end, the proximal end of the distal wire segment comprising a second tongue having a second flat planar bonding face which extends parallel to the longitudinal axis, the distal wire segment having a second elasticity and being formed out of a second material having a second ultimate tensile strength, wherein the second material is different than the first material, and further wherein the second ultimate tensile strength is different than the first ultimate tensile strength;

wherein the second flat planar bonding face of the second tongue of the distal wire segment is formed complementary to the first flat planar bonding face of the first tongue of the proximal wire segment; and bonding the first flat planar bonding face of the first tongue of the proximal wire segment to the complementary second flat planar bonding face of the second tongue of the distal wire segment in an overlapping manner;

wherein the first tongue and the second tongue have complementary but dissimilar cross-sections;

and further wherein the cross-sections of the first and second tongues are set in relation to each other such that a break load of the first tongue is equal to a break load of the second tongue throughout lengths of the bonding faces of the tongues.

* * * * *